United States Patent [19]

Pechersky

[11] Patent Number: 5,520,052
[45] Date of Patent: May 28, 1996

[54] METHOD AND APPARATUS FOR DETERMINING MATERIAL STRUCTURAL INTEGRITY

[75] Inventor: Martin Pechersky, Aiken, S.C.

[73] Assignee: The United States of America as represented by the United States Department of Energy, Washington, D.C.

[21] Appl. No.: 194,432

[22] Filed: Feb. 10, 1994

[51] Int. Cl.$^6$ .................... G01H 9/00; G01H 13/00; G01N 29/12
[52] U.S. Cl. .................................. 73/579; 73/657
[58] Field of Search ....................... 73/579, 581, 582, 73/583, 655, 657, 645, 646, 647, 648, 643

[56] References Cited

U.S. PATENT DOCUMENTS

| | | | |
|---|---|---|---|
| 3,482,436 | 12/1969 | Neish et al. | 73/657 |
| 3,815,407 | 6/1974 | Lavery | 73/582 |
| 4,031,744 | 6/1977 | Flannelly | 73/583 |
| 4,342,229 | 8/1982 | Massa | 73/579 |
| 4,526,465 | 7/1985 | Corti et al. | 356/35.5 |
| 4,641,527 | 2/1987 | Hiroi et al. | 73/582 |
| 4,723,448 | 2/1988 | Veligdan | 73/657 |
| 4,823,601 | 4/1989 | Barna | 73/594 |
| 4,824,250 | 4/1989 | Newman | 356/345 |
| 4,928,527 | 5/1989 | Burger et al. | 73/657 |
| 5,227,982 | 7/1993 | Kipple et al. | 73/579 |
| 5,402,781 | 4/1995 | Dimarogonas | 73/579 |

*Primary Examiner*—Hezron E. Williams
*Assistant Examiner*—Rose M. Finley
*Attorney, Agent, or Firm*—Brian Tumm; Harold M. Dixon; William R. Moser

[57] ABSTRACT

A non-destructive method and apparatus for determining the structural integrity of materials by combining laser vibrometry with damping analysis techniques to determine the damping loss factor of a material. The method comprises the steps of vibrating the area being tested over a known frequency range and measuring vibrational force and velocity as a function of time over the known frequency range. Vibrational velocity is preferably measured by a laser vibrometer. Measurement of the vibrational force depends on the vibration method. If an electromagnetic coil is used to vibrate a magnet secured to the area being tested, then the vibrational force is determined by the amount of coil current used in vibrating the magnet. If a reciprocating transducer is used to vibrate a magnet secured to the area being tested, then the vibrational force is determined by a force gauge in the reciprocating transducer. Using known vibrational analysis methods, a plot of the drive point mobility of the material over the preselected frequency range is generated from the vibrational force and velocity measurements. The damping loss factor is derived from a plot of the drive point mobility over the preselected frequency range using the resonance dwell method and compared with a reference damping loss factor for structural integrity evaluation.

20 Claims, 2 Drawing Sheets

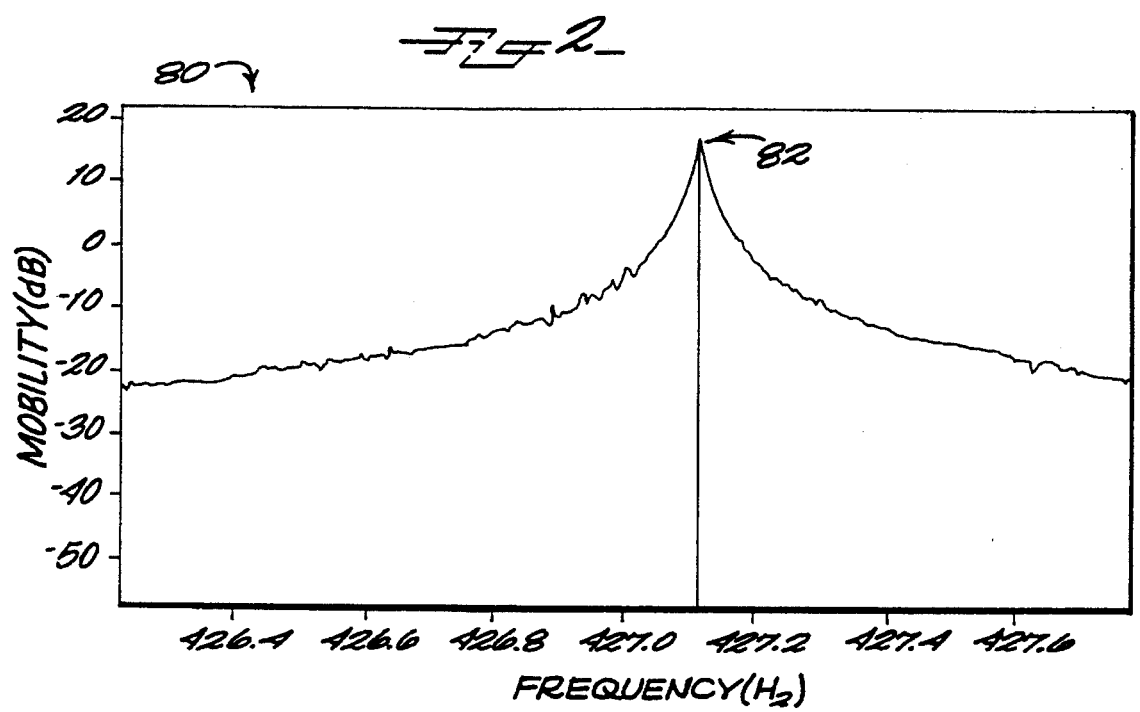

METHOD AND APPARATUS FOR DETERMINING MATERIAL STRUCTURAL INTEGRITY

BACKGROUND OF THE INVENTION

1. Field of the Invention

The present invention relates to non-destructive methods and apparatus for determining the structural integrity of materials. More particularly, the present invention relates to the combination of laser vibrometry and vibrational analysis techniques for determining macro- and microstructural irregularities in materials. The United States Government has rights in this invention pursuant to Contract No. DE-AC09-898R18035 between the U.S. Department of Energy and Westinghouse Savannah River Company.

2. Discussion of Background

Material testing for quality control and related areas continues to be mostly destructive in nature despite efforts to develop non-destructive alternatives that are more feasible in terms of price, convenience and reliability. Although destructive testing is quite often more accurate because the condition of the material is made manifest rather than inferred, the obvious disadvantage is that the material or product tested is destroyed or rendered useless by the testing process.

Most non-destructive testing evaluates material composition and structure by relying on the interaction of the tested material with sound waves or electromagnetic radiation. Such methods involve monitoring the effect of pressure or electromagnetic waves passing through the material as they are influenced by flaws or inhomogeneities in the test structure.

The analysis in most non-destructive testing of this type relies on the relationship between the material's resonant frequency and the strength and quality of the material's structure. The resonant frequency of a material depends upon, among other things, the material's shape, density, stiffness and the like.

Typically, the tested material structure is vibrated using a known force and the vibrational velocity of the tested area is measured. Using known techniques, the data is used to compute the resonant frequency of the tested area. Qualitative evaluations are then made based on the resonant frequency using known relationships.

Means for non-destructively vibrating test objects include gas jets, magnetic fields, acoustic, optical and electro-mechanical waves, all of which are discussed in U.S. Pat. No. 4,641,527, issued to Hiroi, et al. Alternatively, acoustic waves produced by transducers can provide necessary vibration, as disclosed in U.S. Pat. No. 4,824,250, issued to Newman, and U.S. Pat. No. 4,723,448, issued to Veligdan. Suitable vibrational velocity measuring means include laser vibrometers or other means for comparing the direction and reflection of laser beams about a vibrated area. For example, see U.S. Pat. No. 3,482,436, issued to Neish, et al. for a vibration-responsive apparatus.

Laser beams are known for use in non-destructive testing to detect structural defects. For example, in U.S. Pat. No. 3,604,253, a laser beam is projected onto a test object, the object is vibrated and the pattern of light reflected from the object is analyzed. As the frequency and intensity of vibrations are varied, changes appear in the pattern of light, thus indicating defects in the object. Also, J. W. Lemmens, Inc. has developed a non-destructive materials testing system that makes use of the relationship between resonant frequency and the structural soundness of materials.

A less common characteristic feature used in non-destructive testing of material structures is the phenomenon of damping. Damping, in general, refers to a material's ability to absorb externally-induced vibration due to its microstructure. Measurements of damping characteristics, such as damping factors and damping loss factors, are typically used in vibration control applications. Damping loss factors have not been used in determining or evaluating the strength, degree of abnormalities or overall quality in material structures and bonded areas between structures, such as solder joints, welds and the like.

Vibrational analysis methods for measuring damping characteristics of materials, such as the resonance dwell method, are well known for vibrational control applications. In the resonance dwell method, the damping loss factor is determined from the width of the mobility curve as a function of frequency at the half power points. In short, the width of the mobility curve at this point divided by the resonant frequency around which the mobility curve is plotted, yields the damping loss factor of the inspected area.

There is a need for a more effective, non-destructive testing method for determining the integrity of material structures and bonding means therebetween.

SUMMARY OF THE INVENTION

According to its major aspects and broadly stated, the present invention is a non-destructive method and apparatus for determining the structural integrity of materials and components. In particular, the present invention combines laser vibrometry with damping analysis techniques to determine the damping loss factor of a material or component, preferably materials such as the pinch weld of reservoir fill stems. The method comprises the steps of vibrating the area being tested over a known frequency range and measuring vibrational force and velocity as a function of time over the known frequency range. Vibrational velocity is preferably measured by a laser vibrometer, but can be measured by any non-contacting means having equivalent measurement accuracy. Measurement of the vibrational force depends on the vibration method. If an electromagnetic coil is used to vibrate a magnet secured to the area being tested, then the vibrational force can be determined by the amount of coil current used in vibrating the magnet. If a reciprocating transducer is used to vibrate a magnet secured to the area being tested, then the vibrational force can be determined by a force gauge in the reciprocating transducer. Using known vibrational analysis, a plot of the drive point mobility of the material over the preselected frequency range is generated from the vibrational force and velocity measurements. The damping loss factor, which is related to the structural integrity of the material, is derived from the drive point mobility plot using the resonance dwell method. Once computed, the damping loss factor can be compared with a reference damping loss factor to evaluate the structural integrity of the material.

A major feature of the present invention is the use of vibrational analysis, specifically, the determination of the damping loss factor, for structural integrity evaluation. In the prior art, damping and vibration analysis are used in vibration control. Also, structural integrity analysis typically makes use of the correlation between the resonant frequency of an object and its structural quality. The advantage of using damping analysis for structural integrity evaluation is that the structural integrity of an object can be determined non-destructively. Further, currently available equipment, such as laser vibrometers, allows the damping analysis to be performed quickly, accurately and, if desired, remotely. Determining the damping loss factor of an object offers a qualitative and quantitative measurement of structural integrity. Furthermore, the damping loss factor can be determined very quickly using known analysis techniques in conjunction with available curve-fitting software.

Another feature of the present invention is the use of a laser vibrometer for determining vibrational velocity, which is used in computing the damping loss factor and thus for evaluating the overall structural integrity of the object being tested. The laser vibrometer transmits laser light to the vibrated area and collects laser light scattered or reflected therefrom. Comparisons of the transmitted light with the scattered light results in wavelength interference related to the vibrational velocity of the vibrated area. The laser vibrometer is more accurate and convenient than other devices for measuring vibrational velocity. Also, the laser vibrometer is non-contacting and thus does not corrupt or confound the damping data of the object being tested. The laser vibrometer is especially convenient in that laser light can be transmitted and collected from a remote location, thus allowing inspection of materials in hazardous or difficult to reach locations.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 2 is a graph of drive point mobility as a function of frequency of a test material according to the test arrangement of FIG. 1.

DETAILED DESCRIPTION OF A PREFERRED EMBODIMENT

Figure 1:
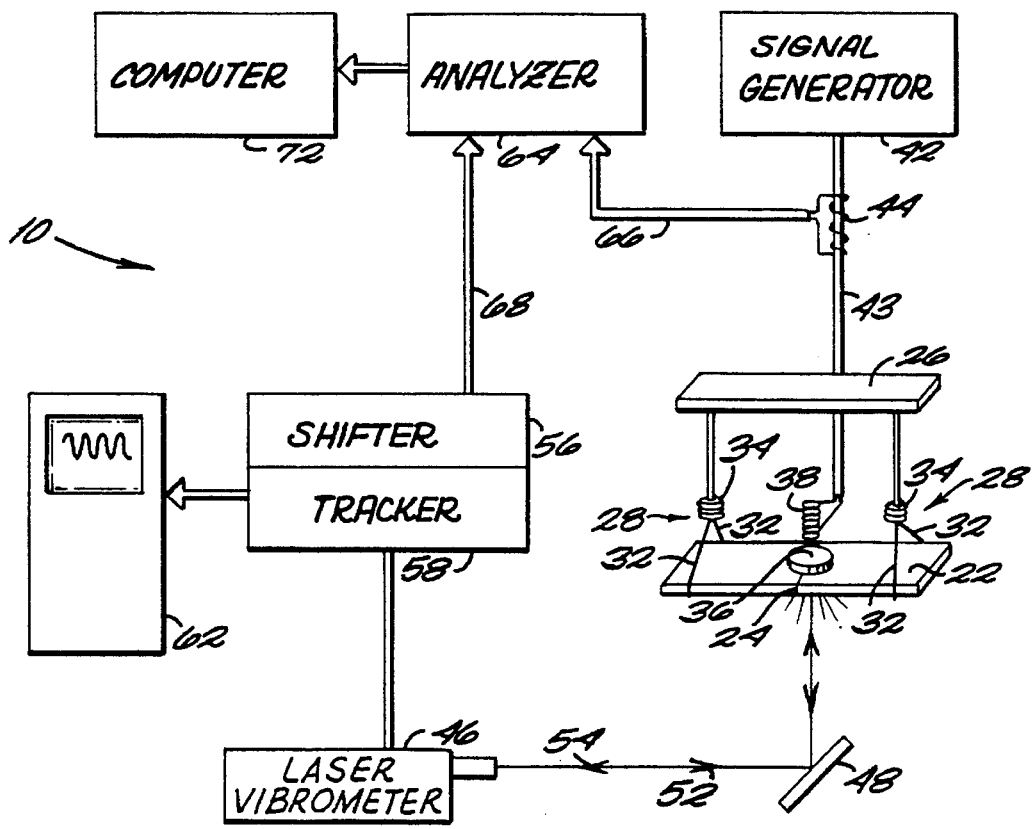
FIG. 1 is a schematic diagram of a test arrangement demonstrating the present invention.

In the following description similar components are referred to by the same reference numeral in order to simplify the understanding of the sequential aspect of the drawings.

The present invention uses the damping loss factor of a material to determine qualitatively the structural integrity of a material. "Structural integrity" refers generally to its soundness, or, more specifically, to the absence of macro- and microstructural irregularities that are known or suspect to affect the strength of the material. In this manner, anelastic properties of materials such as weld locations, structures made by precision casting operations and the like are determined using known measuring devices in combination with standard digital analysis techniques normally used in vibration control analysis.

The damping loss factor, in general, is an indication of a material's ability to absorb vibrations. The presence of microscopic cracks, voids, dislocations and other irregularities generally enhances a material's ability to absorb vibrations, but is also considered adverse to the overall strength and quality of the macro- and microstructure. Thus, the damping loss factor of a material provides an indication of the overall quality of the material's structural integrity. A material of relatively high quality will have fewer structural irregularities, will not absorb vibration as well and thus will have a lower damping loss factor than a relatively poor quality material having significantly more structural irregularities. Therefore, the damping loss factor is directly related to the structural integrity of a material.

The damping loss factor, once determined, can be compared to known standards of reference materials or used with other measurements in determining the nature of a material's structural integrity. For example, in welded structures, if the weld is of high quality, then the damping loss factor will be very close to or indistinguishable from the base material. If there are defects or inhomogeneities in the weld microstructure, then the damping loss factor will be larger. Similar observations are true for single-piece materials formed by precision casting operations.

Typically, damping factors in metals are low and changes in them due to a defective weld may increase the damping loss factor of the structure by a factor of 2 or 3. However, since the damping loss factor is usually on the order of parts per million (ppm), a damping loss factor increased by a factor of 3 will still be a very small number. Thus, it is necessary that the damping loss factor to be measured with high degree of accuracy, such as with a non-contacting method.

Because the damping loss factor of a material can vary simply by the nature or orientation of its support mechanism, measuring the damping loss factor accurately involves the elimination or minimization of such external factors. Thus, a material must be supported or bound at its nodes, that is, where the vibrations are effectively "zeroed out" and have virtually no amplitude. Moreover, to insure the highest degree of accuracy, a complete modal analysis of the material being tested should be performed for each different material shape.

Also, it is necessary that the resonant frequency of the material being tested be known in order to establish proper testing parameters. Usually, the resonant frequency is known via previous testing methods or theoretical analysis. Also, with precision cast or machined materials, an initial resonant frequency determination is sufficient since precision cast materials produced subsequently are nearly identical in size, shape and density.

Referring now to FIG. 1, an experimental arrangement of the present invention is shown schematically. In the experimentation, the material being tested is a slender metal bar 22 formed from two pieces welded together as shown by weld 24 (in actuality, weld 24 cannot be seen by the human eye). Preferably, metal bar 22 is approximately 20 cm in length and has a rectangular cross-section whose width is approximately 1 cm and whose thickness is approximately 0.5 cm, although bars of other sizes have been tested and are quite adequate. For experimental purposes, metal bar 22 is preferred because it's relatively simple shape has well known mode shapes and resonance frequencies.

Metal bar 22 is suspended from a support 26 by a vibrationally-isolated means (shown generally as 28) in the form of silk threads 32 attached to springs 34 having spring constants chosen to provide adequate vibration isolation from support 26. Thus, in this arrangement, metal bar 22 is vibrationally isolated.

Next, a small magnet 36 is glued to metal bar 22 at weld 24. An electromagnetic coil 38, connected to a signal generator 42 through an electrical conductor 43, is positioned in close proximity to magnet 36 so that when signal generator 42 passes a sufficient amount of current through electromagnetic coil 38, the magnetic field thus created vibrates magnet 36. The vibrational force with which magnet 36 is vibrated is related to and easily determined from the amount of current passing through electromagnetic coil 38. Thus, a current probe 44 is operably positioned to measure the amount of current passing through electromagnetic coil 38.

In order to measure the vibrational velocity at weld 24, a laser vibrometer 46 in cooperation with a reflecting means 48, preferably a mirror, is used to direct a beam of laser light transmitted from laser vibrometer 46 (shown generally as 52) at weld 24. Laser vibrometer 46 also collects the laser light that is scattered or reflected by weld 24 (shown generally as 54).

Measuring vibrational velocity using a laser vibrometer is based on the measurement of the very slight shift in the wavelength of laser light when it scatters or is reflected from a moving object. Combining the transmitted light with the scattered light causes interference, which interference is related to the amount of the shift and thus related to the vibrational velocity of the area on which the laser light is directed.

Referring again to FIG. 1, a frequency shifter 56 and a frequency tracker 58 are operably connected to laser vibrometer 46. Frequency shifter 56 shifts the frequency of laser light beam 52 being transmitted by laser vibrometer 46 in known increments and over a preselected frequency range. Frequency tracker 58 monitors the frequency shifts of laser light beam 52 transmitted by laser vibrometer 46 as well as the interference created when the transmitted and reflected laser light are combined. Frequency tracker 58 uses the degree of interference to generate a voltage signal proportional to the vibrational velocity at weld 24. Preferably, an oscilloscope 62 is used to monitor raw data from frequency tracker 58.

Vibrational force measurements taken by current probe 44 and vibrational velocity measurements observed by laser vibrometer 46, frequency tracker 58 and frequency shifter 56 are fed into an analyzer 64 (as shown by lines 66 and 68, respectively). Preferably, analyzer 64 is a Fast Fourier Transform (FFT) analyzer, which transforms the time-varying vibrational force (t) and velocity v(t) measurements into the frequency domain as F(f) and v(f), respectively. Using analyzer 64, the Transforms are computed very rapidly. Then, analyzer 64 takes the ratio of the Transforms, known as the drive point mobility, and displays the magnitude and phase. From this display, the resonant frequencies of metal bar 22 are easily identified as the periodic peaks in the display.

From this display, a particular resonant frequency is chosen and the experimental procedures are repeated, except using a much smaller frequency range centered around the chosen resonant frequency. For example, in actual experimentation using the arrangement as shown in FIG. 1, the resonant frequency for the second mode of metal bar 22 was found to be 427.117 Hz. Using this resonant frequency, the time-varying vibrational force f(t) and velocity v(t) were measured over a frequency range from approximately 426.2 Hz to approximately 427.8 Hz. The Transforms of f(t) and v(t) were computed and the ratio of the Transforms (also known as drive point mobility) was determined over the preselected frequency range. A computer 72 connected to analyzer 64 was used to plot the mobility over the preselected frequency range, as shown by graph 80 in FIG. 2. A peak 82 in the graph 80 represents the preselected resonant frequency (in this case 427.117 Hz).

The damping loss factor is computed from the shape of the mobility curve over the preselected frequency range. Specifically, the damping loss factor is computed by locating the center frequency (corresponding to the resonant frequency and shown as a peak on the drive point mobility plot of FIG. 2) and dividing the half power bandwidth (−3 dB) of the curve by that frequency. Such analysis techniques are well known and can be found in various references discussing modal analysis techniques, such as *Vibration Damping*, by A. D. Nashif, D. I. G. Jones and J. P. Henderson.

For the experimental arrangement illustrated in FIG. 1, the frequency range was approximately 1.95 mHz. The half power points were 427.105 Hz and 427.123 Hz for a bandwidth of 18 mHz and a damping loss factor of 0.000042 or 42 ppm (18 mHz/427.113 Hz).

As mentioned previously, the damping loss factor of a material is derived from the drive point mobility over a preselected frequency range. To determine the drive point mobility accurately, especially in low damped systems where the damping loss factor will be low, noise must be minimized in the measurement process. Also, extraneous energy losses must be minimized in both the excitation and measurement process. However, the nature of the experimentation is such that bias errors will not contribute to errors in the measurement. That is, the random noise is translated into an increased half power bandwidth during the Fourier Transform operation. Also, fixed errors in the force or velocity will be reflected by a scale shift, but not a shift in bandwidth or center frequency. Therefore, as long as the errors remain fixed during the measurement process, the end result will not be affected.

Energy losses in the system can be introduced in one of many forms, including air damping, vibrational excitation of the support system, dissipation in the supports and dissipation due to air friction. Also apparent losses can result from modal overlap when an excitation frequency is near the resonance frequencies of more than one mode.

Ideally, all of the sources of errors are identified and made sufficiently small. However, since it is impossible to eliminate all of the error sources present, the objective is to minimize their effects so that changes in damping from one test article to another of the same size, shape and material can be determined.

Figure 3:
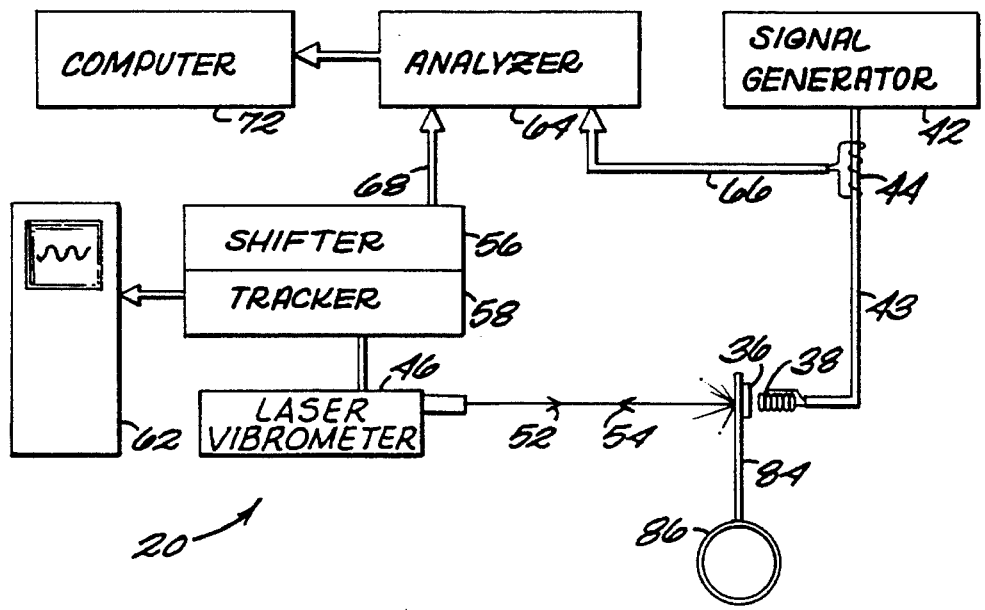
FIG. 3 is a schematic diagram of the present invention according to a preferred embodiment.

FIG. 3 illustrates a schematic representation of a suitable arrangement 20 for the present invention in evaluating the structural integrity of a pinch weld in a fill stem 84 of a reservoir 86. Due to the need for minimizing external errors, reservoir 86 is mounted on a low friction, vibrationally isolated suspension system (not shown). Such a suspension system would depend on the size and shape of reservoir 86, but one of suitable means is preferably a set of diamond or air bearings.

Similar to the experimental arrangement shown in FIG. 1, magnet 36 is positioned in direct contact with one side of fill stem 84 and electromagnetic coil 38 is positioned in close proximity to magnet 36 so that magnet 36 vibrates when signal generator 42 passes current through electromagnetic coil 38 to create an electric field having sufficient strength. Alternatively, any suitable non-contacting device having a measurable vibrational force can be used to vibrate magnet 36 instead of electromagnetic coil 38. For example, a reciprocating transducer (not shown) can be positioned in contact with magnet 36 and displacement of the transducer can be correlated to the amount of vibrational force being applied to magnet 36. As previously discussed, the vibrational force supplied by electromagnetic coil 38 to magnet 36 is related to the amount of coil current passing through electromagnetic coil 38.

Laser vibrometer 46 is preferably positioned to direct transmitted laser light beam 52 at fill stem 84 at a location opposite to magnet 36. Laser vibrometer 46 also collects laser light 54 scattered or reflected by fill stem 84. As discussed previously, the wavelength of the scattered light has been shifted slightly and the degree of interference created by combining transmitted light 52 with scattered light 54 is related to the vibrational velocity at the area of interest, in this case, along fill stem 84.

Frequency shifter 56, frequency tracker 58 and oscilloscope 62 perform in the same way as described above in the experimental arrangement of FIG. 1. Also, analyzer 64 is fed measurements from current probe 44 relating to vibrational force and voltage signals from frequency tracker 58 relating to vibrational velocity. FFT analyzer 64 and computer 72 combine to determine and plot the drive point mobility and ultimately the damping loss factor, in the manner as discussed above.

The process is almost instantaneous since the Fourier Transforms and the ratio of Transforms are computed in near real-time by analyzer 64 and rapid curve fitting routines are available for computer 72 to calculate the damping loss factor once the input data has been received by computer 72 from analyzer 64.

It will be apparent to those skilled in the art that many changes and substitutions can be made to the preferred embodiment herein described without departing from the spirit and scope of the present invention as defined by the appended claims.

What is claimed is:

1. A method for evaluating the structural integrity of a sample of a material by the sample's damping loss factor, said method comprising the steps of:

isolating vibrationally said sample;

vibrating a portion of said sample at a point remote from a suspension point of said sample over a preselected range of frequencies by applying sufficient vibrational force at each frequency in said preselected range of frequencies to vibrate said portion, said portion vibrating at a different vibrational velocity at each frequency;

measuring vibrational velocity as a function of time of said sample over said preselected range of frequencies to generate a plurality of vibrational velocity measurements;

computing a drive point mobility of said sample over said preselected range of frequencies, said drive point mobility derived from said pluralities of vibrational force and velocity measurements;

computing a damping loss factor of said sample from said drive point mobility; and comparing said damping loss factor of said sample with a reference damping loss factor for said material to determine whether said sample behaves differently than said reference material.

2. The method as recited in claim 1, wherein said drive point mobility computing step further comprises the steps of:

transforming said plurality of vibrational force measurements from said function of time to a function of frequency;

transforming said plurality of vibrational velocity measurements from said function of time to a function of frequency; and computing the ratio of said vibrational force measurements as a function of frequency to said vibrational velocity measurements as a function of frequency over said preselected range of frequencies.

3. The method as recited in claim 1, wherein said vibrational velocity measuring step further comprises the steps of:

directing laser light at said portion of said sample;

collecting said laser light scattered from said portion of said sample so that said scattered laser light creates an interference with said directed laser light, said interference related to said vibrational velocity; and determining said vibrational velocity from said interference.

4. The method as recited in claim 1, wherein said vibrating step further comprises the steps of:

placing a magnet on said portion of said sample; and creating a magnetic field near said magnet so that said magnet vibrates whereby said portion of said sample vibrates in accordance with said magnetic field.

5. The method as recited in claim 1, wherein said vibrating step further comprises the steps of:

placing a magnet on said portion of said sample; and creating a magnetic field near said magnet with a current in a coil so that said magnet vibrates whereby said portion of said sample vibrates in accordance with said magnetic field, and wherein said vibrational force measuring step includes the step of measuring an amount of said coil current.

6. The method as recited in claim 1, wherein said vibrating step further comprises the steps of:

placing a magnet on said portion of said sample;

placing a reciprocating transducer on said magnet; and exciting said reciprocating transducer to vibrate said reciprocating transducer and said magnet whereby said portion of said sample is vibrated in accordance with excitation of said reciprocating transducer.

7. The method as recited in claim 1, wherein said vibrating step further comprises the steps of:

placing a magnet on said portion of said sample;

placing a reciprocating transducer on said magnet; and exciting said reciprocating transducer to vibrate said reciprocating transducer and said magnet whereby said portion of said sample is vibrated in accordance with excitation of said reciprocating transducer, and wherein said vibrational force measuring step includes the step of measuring vibration of said reciprocating transducer.

8. The method as recited in claim 1, wherein said material has a resonant frequency and wherein said preselected frequency range includes said resonant frequency.

9. The method according to claim 1, wherein said step of isolating vibrationally said sample further comprises the step of:

suspending said sample along a node of said sample.

10. A method for evaluating the structural integrity of a sample of a material by the sample's damping loss factor, said sample having a resonant frequency, said method comprising the steps of:

providing a sample supported along a node of said sample;

vibrating said sample over a preselected range of frequencies including said resonant frequency by applying vibrational force at a point remote from said support and sufficient to vibrate said sample at each frequency in said range of frequencies;

measuring vibrational force as a function of time of said sample over said preselected range of frequencies to generate a plurality of vibrational force measurements;

transforming said plurality of vibrational force measurements from said function of time to a function of frequency;

measuring the vibrational velocity as a function of time of said sample over said preselected range of frequencies to generate a plurality of vibrational velocity measurements;

transforming said plurality of vibrational velocity measurements from said function of time to a function of frequency;

computing a ratio of said transformed vibrational force measurements to said transformed vibrational velocity measurements;

computing a damping loss factor of said sample from said ratio, and comparing said damping loss factor of said sample to a reference damping loss factor of a said material.

11. The method as recited in claim 10, wherein said vibrational velocity measuring step further comprises the steps of:

directing laser light at said sample;

combining said laser light scattered from said sample with said directed laser light to produce an interference, said interference being related to said vibrational velocity; and determining said vibrational velocity from said interference.

12. The method as recited in claim 10, wherein said vibrating step further comprises the steps of:

placing a magnet on said sample; and creating a magnetic field near said magnet so that said magnet vibrates whereby said sample vibrates in accordance with said magnetic field.

13. The method as recited in claim 10, wherein said vibrating step further comprises the steps of:

placing a magnet on said portion of said sample; and creating a magnetic field near said magnet with a current in a coil so that said magnet vibrates whereby said portion of said sample vibrates in accordance with said magnetic field, and wherein said vibrational force measuring step includes the step of measuring an amount of said coil current.

14. The method as recited in claim 10, wherein said vibrating step further comprises the steps of:

placing a magnet on said sample;

placing a reciprocating transducer on said magnet; and exciting said reciprocating transducer to vibrate said reciprocating transducer and said magnet whereby said sample is vibrated in accordance with excitation of said reciprocating transducer.

15. The method as recited in claim 10, wherein said vibrating step further comprises the steps of:

placing a magnet on said sample;

placing a reciprocating transducer on said magnet; and exciting said reciprocating transducer to vibrate said reciprocating transducer and said magnet whereby said sample is vibrated in accordance with excitation of said reciprocating transducer, and wherein said vibrational force measuring step includes the step of measuring vibration of said reciprocating transducer.

16. Apparatus for evaluating the structural integrity of a sample of a material including a weld by the sample's damping loss factor, said sample having a resonant frequency, said apparatus comprising:

means for positioning said sample in an essentially vibration-free manner along a node of said sample;

means for vibrating said sample over a preselected range of frequencies including said resonant frequency by applying a vibrational force to said sample;

means responsive to said vibrating means for measuring said vibrational force applied to said sample by said vibrating means, said vibrational force measuring means generating a plurality of vibrational force measurements as a function of time;

means responsive to said vibrating sample for measuring a vibrational velocity of said sample, said vibrational velocity measuring means generating a plurality of vibrational velocity measurement as a function of time;

means operably connected to said vibrational force measuring means and said vibrational velocity measuring means for calculating a damping loss factor of said sample from said plurality of vibrational force and velocity measurements and comparing said damping loss factor of said sample to a reference damping loss factor of said material to indicate structural integrity of said sample.

17. The apparatus as recited in claim 16, wherein said calculating and comparing means further comprises:

first means for transforming said plurality of vibrational force measurements from functions of time to functions of frequency;

second means for transforming said plurality of vibrational velocity measurements from functions of time to functions of frequency;

means for computing a drive point mobility of said sample over said preselected frequency range from said transformed vibrational force measurements and said transformed vibrational velocity measurements, said first computing means generating a plurality of drive point mobility computations; and means for computing said damping loss factor from said plurality of drive point mobility computations for comparison to a reference damping loss factor for said material to indicate structural integrity of said sample.

18. The apparatus as recited in claim 16, wherein said vibrational velocity measuring means further comprises a laser vibrometer, said laser vibrometer directing laser light at said sample and collecting laser light scattered from said sample, said laser vibrometer determining the velocity of said vibrations based on interference of said collected laser light with said directed laser light.

19. The apparatus as recited in claim 16, wherein said vibrating means further comprises:

a magnet placed on said sample; and a coil near said magnet for conducting an electric current, said coil creating a magnetic field near said magnet that vibrates said magnet and said sample, said vibrational force being related to said current.

20. The method as recited in claim 16, wherein said vibrating means further comprises:

a magnet placed on said sample; and a coil near said magnet for conducting an electric current, said coil creating a magnetic field near said magnet that vibrates said magnet and said sample, said vibrational force being related to said current, and wherein said vibrational force measuring means further comprises a current probe for measuring said current.

* * * * *